United States Patent [19]
Ita et al.

[11] Patent Number: 5,106,982
[45] Date of Patent: Apr. 21, 1992

[54] PIPERIDINYL CARBONYL DERIVATIVES

[75] Inventors: Callixtus E. Ita, South River; Peter Egli, Titusville, both of N.J.

[73] Assignee: E. R. Squibb & Sons, Inc., Princeton, N.J.

[21] Appl. No.: 625,333

[22] Filed: Dec. 10, 1990

[51] Int. Cl.$^5$ .................. C07D 211/60; C07D 401/06
[52] U.S. Cl. ...................... 546/208; 546/22; 546/24; 546/242; 546/245
[58] Field of Search .................. 546/22, 24, 208, 242, 546/245

[56] References Cited
U.S. PATENT DOCUMENTS

| | | | |
|---|---|---|---|
| 4,154,960 | 5/1979 | Ondetti et al. | 562/426 |
| 4,470,973 | 9/1984 | Natarajan et al. | 546/146 X |

*Primary Examiner*—Richard L. Raymond
*Attorney, Agent, or Firm*—Theodore R. Furman, Jr.

[57] ABSTRACT

Novel compounds having the general formula

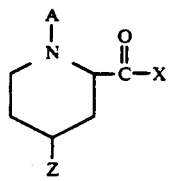

Ia or

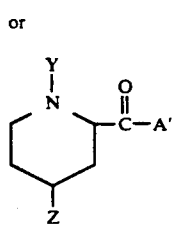

Ib wherein A and A' are amino acid residues linked by a peptidal bond to the nucleus, are disclosed. These compounds are CNS agents with anxiogenic activity.

3 Claims, No Drawings

PIPERIDINYL CARBONYL DERIVATIVES

SUMMARY OF THE INVENTION

In accordance with the present invention novel compounds active on the central nervous system and useful, for example, as anxiogenic agents, are disclosed. The compounds of this invention have the general formula

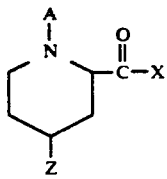

Ia or

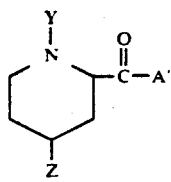

Ib wherein A and A' are amino acid radicals linked by a peptidal bond to the

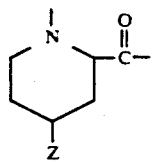

nucleus; and wherein
X is —OR, —PHO$_3$ or —NH$_3$;
Y is hydrogen or alkyl;
Z is hydrogen or —SO$_2$OH; and,
R is hydrogen or alkyl.

DETAILED DESCRIPTION OF THE INVENTION

The present invention in its broadest aspects relates to compounds of formula Ia and Ib. These compounds are useful as central nervous system (CNS) agents and have particular suitability as cognition enhancers.

The term "alkyl" as it is used throughout this application refers to straight or branched chain radicals having 1 to 12 carbons, with 1 to 8 carbons being preferred.

The term "amino acid radicals linked by a peptidal bond" refers to amino acid radicals and amino acid derivative radicals linked to the nucleus

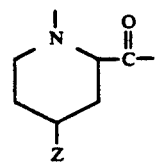

via a

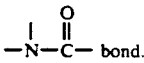

bond.

Suitable amino acid radicals for A include

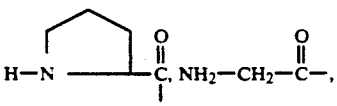

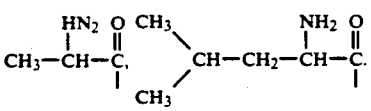

Suitable amino acid radicals for A' include

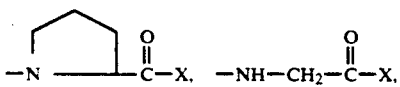

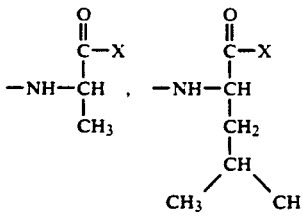

wherein X, as defined above, is —OR, —PHO$_3$, or —NH$_3$ and R is hydrogen or alkyl.

To prepare the compounds of formula Ib, a compound of the formula

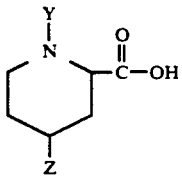

is treated with a protective agent, such as benzylchloroformate and a base such as potassium carbonate in solvents, e.g. acetone and water, to provide a compound of the formula

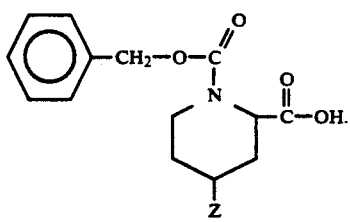

B

Compound B is thereafter coupled with an amino acid of the formula

H—A'  (C)

or a protected form thereof, in the presence of a dehydrating agent, such as hydroxybenzotriazole hydrate, an organic base such as triethylamine and a coupling agent such as a carbodiimide, and in a solvent such as dimethylformamide to provide a compound of the formula

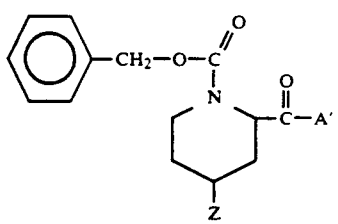

(which may include protection at the carboxylic group within the amino acid radical, A′).

Compound D is thereafter reduced (deprotected) by treatment with hydrogen gas in a solvent, e.g. methanol, in the presence of a catalyst, e.g., palladium on carbon, to provide compounds of the formula

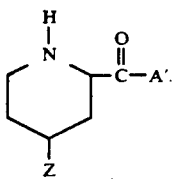

Compounds of formula Ib where Y is other than hydrogen can therafter be prepared by reacting a compound of the formula

Y—H                                            (F)

with compound E in dimethylformamide and in the presence of a dehydrating agent, as described above.

In a corresponding manner, compounds of formula Ia can be prepared by protecting the carbonyl terminus of

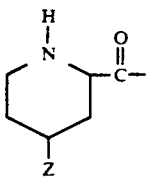

and thereafter reacting with a compound of the formula H—A and thereafter X—H as described above.

As described above, the present compounds are useful in that they act on the central nervous system. They have utility, for example, as anxiogenic agents and are useful therefore as cognition enhancers.

The compounds of the invention can be administered orally, parenterally or transdermally to various mammalian species in need of such agents, e.g., humans, cats, dogs, and the like, in an effective amount within the dosage range of about 1 to 100 mg/kg on a regimen in single or 2 to 4 divided daily doses.

The active substance can be utilized in a composition such as tablet, capsule, solution, suspension or transdermal patch containing about 5 to about 500 mg per unit of dosage of a compound or mixture of compounds of formula Ia and Ib. They may be compounded in conventional matter with a physiologically acceptable vehicle or carrier, excipient, binder, preservative, stabilizer, flavor, etc., as called for by accepted pharmaceutical practice.

Preferred compounds of the present invention are those wherein A is a radical form of proline, glycine, alanine or p-amionbutyric acid.

Most preferred are the compounds of formula Ib wherein A′ is

The present invention will now be further described by the following examples.

EXAMPLE 1

1-(2-Piperidinylcarbonyl)-L-proline

A. 1,2-Piperidinedicarboxylic acid, 1-(phenylmethyl) ester

To potassium carbonate (16.1 g, 116.1 mmol) in acetone (550 ml) and water (150 ml) at 0° C. was added DL-Pipecolinic acid (5.0 g, 38.7 mmol) and stirred until dissolved. Benzyl chloroformate (7.26 g, 42.6 mmol) was then added at 0° C. and the reaction solution was stirred for 4 hours while slowly warming to room temperature. Most of the acetone was removed under reduced pressure. The pH of the residual aqueous liquid was adjusted to 2.0 before extraction with ethyl acetate (3×200 ml). The combined extracts were washed with brine (1×100 ml), dried over anhydrous magnesium sulfate, filtered and concentrated. The crude viscous yellow liquid was purified by chromatography on a silica gel column and eluted with 50 percent ethyl acetate in hexane to yield the title A compound (8.40 g) as a viscous colorless liquid.

B. 1-[[1-[(Phenylmethoxy)carbonyl]-2-piperidinyl]carbonyl]-L-proline, phenylmethyl ester.

To dimethylformamide (anhydrous, 25 ml) at 0° C. was added the title A compound (2.0 g, 7.60 mmol), 1-hydroxybenzotriazole hydrate (1.28 g, 7.60 mmol) and L-proline benzyl ester hydrochloride (2.84 g, 7.60 mmol) and stirred until dissolved. Triethylamine (3.20 ml, 2.31 g, 22.8 mmol) was added and stirred for 5 minutes. Next, 1-(3-dimethylaminopropyl)-3-ethylcarbodiimide hydrochloride (1.46 g, 7.60 mmol) was added and the reaction mixture was stirred for 16 hours while warming to room temperature. The dimethylformamide was removed under reduced pressure and the residue was dissolved in 1N hydrochloric acid (20 ml), extracted with methylene chloride (2×20 ml), dried over anhydrous magnesium sulfate, filtered and concentrated. The crude brown oil was chromatographed on a silica gel column and eluted with 0-1 percent methanol in methylene chloride to obtain the title B compound (1.72 g) as a pale yellow liquid.

C. 1-(2-Piperidinylcarbonyl)-L-proline

The title B compound (1.70 g, 3.77 mmol) and 10% palladium on activated carbon (0.50 g) was added to methanol (20 ml) at room temperature. The atmosphere in the reaction flask was replaced by hydrogen gas at 1 atmosphere using three evacuation/fill cycles. The reaction mixture was stirred vigorously for 2 hours. A total of 132 ml of hydrogen gas was consumed. The hydrogen was removed and the reaction mixture was filtered to remove the catalyst before the solvent was removed under reduced pressure to yield the title compound (0.84 g) as an oil. The oil was dissolved in 2 ml of ethyl ether and crystallized by the gradual addition of 3 ml of ethyl acetate over 30 minutes. After forming overnight, the fine white crystals were filtered and rinsed with ethyl acetate:ethyl ether (10:1, 3 ml), then dried in vacuum to obtain the title compound (0.263 g), m.p.=181° C., as a white crystalline solid.

Analysis calc'd for $C_{11}H_{18}N_2O_3$: C, 58.39, H, 8.02; N, 12.38; Found: C, 58.11; H, 8.07; N, 12.17.

EXAMPLE 2

As a measure of anxiety, the two compartment model of Crawley and Goodwin *Biochemic. Behav.*, 13:167-170 (1980) is often used. The usefulness of this model is based on the natural tendency of mice to explore a novel environment. Using this model as further described by Kilfoil et al. (*Neuropharmacology*, Vol 28, No. 9, p. 901-905 (1989)), the anxiogenic activity of the compound of Example 1 was determined.

Experimental Animals

Mice, 22-25 g were used. Six mice were randomly selected from a group of 10 that were housed in a controlled area for temperature. Lights were on at 6 a.m. and off at 6 p.m. The experiment was done more than 7 days after the mice arrived at the site.

Two Compartment Exploratory Test

The apparatus used was similar to the one described by Crawley and Goodwin. Briefly, this was a paper box that was divided into two chambers. One chamber was covered and the inside painted black (8"×4½"×10¼"). This had an opening of 1½"×1½" into the lighted or open area. The open area (4½"×8½"×10¼") was white. The test was run with a fluorescent laboratory ceiling light directly above the box. The test started at 11:30 a.m. and ended at 6:00 p.m.

Drug and Dose

The compound of Example 1 was dissolved in water to give a concentration of 2 mg/ml. Each mouse received 0.5 ml of this solution (eq. to 40 mg/kg dose) intraperitoneally.

Experimental Design

Animals were picked at random from the 10 mice, marked and dosed with either the drug or water. After dosing, the test animal was returned to the group and left there for 20 minutes; after which time it was then taken from the group and placed in the center of the open chamber of the test apparatus. Timing was started immediately. This was done with a stop/timer with a digital display. One mouse was handled at a time and observation was done over a 60 minute period. The time each mouse spent in the dark area and in the light area was recorded. The results are summarized in the TABLE.

TABLE

| Mouse | # of Shuttles | | Time in Dark(s) | | Time in Light(s) | |
|---|---|---|---|---|---|---|
|  | 10 mins. | 30 mins. | 10 mins. | 30 mins. | 10 mins. | 30 mins. |
| C-1 | 42 | 118 | 232 | 623 | 365 | 1063 |
| C-2 | 18 | 80 | 297 | 1004 | 338 | 761 |
| C-3 |  | 58 |  | 891 |  | 952 |
| T-1 | 4 | 71 | 476 | 1409 | 15 | 471 |
| T-2 | 30 | 62 | 457 | 1470 | 152 | 339 |
| T-3 |  | 50 |  | 1226 |  | 479 |

C = control
T = test

What is claimed is:
1. A compound of the formula

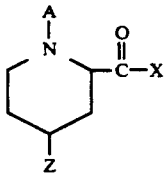  Ia or

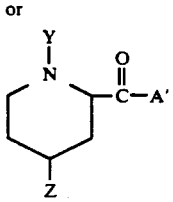  Ib where A can be

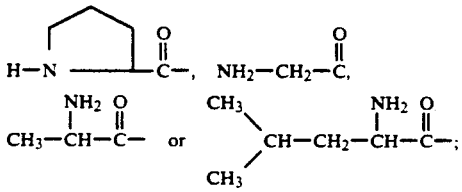

A' can be

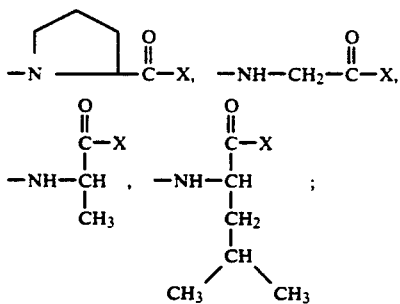

X can be —OR or —$NH_2$;
Y is hydrogen or alkyl;
Z is hydrogen or —$SO_2OH$; and
R is hydrogen or alkyl.
2. The compound of claim 1 formula Ib wherein A' is selected from

3. The compound of claim 1 having the formula

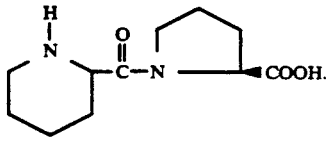

* * * * *